(12) United States Patent
Tao et al.

(10) Patent No.: US 10,961,570 B2
(45) Date of Patent: Mar. 30, 2021

(54) HIGH-THROUGHPUT AND RAPID NUCLEIC ACIDS DETECTION METHOD BASED ON CAPILLARY MICROARRAYS

(71) Applicant: SHANGHAI JIAO TONG UNIVERSITY, Shanghai (CN)

(72) Inventors: Shengce Tao, Shanghai (CN); Litao Yang, Shanghai (CN); Ning Shao, Shanghai (CN); Jiaying Hu, Shanghai (CN); Jianwei Chen, Shanghai (CN); Dabing Zhang, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 276 days.

(21) Appl. No.: 15/777,671

(22) PCT Filed: Apr. 2, 2016

(86) PCT No.: PCT/CN2016/078408
§ 371 (c)(1),
(2) Date: May 21, 2018

(87) PCT Pub. No.: WO2017/096737
PCT Pub. Date: Jun. 15, 2017

(65) Prior Publication Data
US 2019/0119722 A1    Apr. 25, 2019

(30) Foreign Application Priority Data

Dec. 8, 2015 (CN) .......................... 201510901558.1

(51) Int. Cl.
| | |
|---|---|
| *C12Q 1/686* | (2018.01) |
| *C12Q 1/68* | (2018.01) |
| *B01L 3/00* | (2006.01) |
| *C12Q 1/6806* | (2018.01) |
| *B01L 7/00* | (2006.01) |
| *C12Q 1/6853* | (2018.01) |
| *C12Q 1/6874* | (2018.01) |

(52) U.S. Cl.
CPC .......... *C12Q 1/686* (2013.01); *B01L 3/50857* (2013.01); *B01L 7/52* (2013.01); *C12Q 1/68* (2013.01); *C12Q 1/6806* (2013.01); *C12Q 1/6853* (2013.01); *C12Q 1/6874* (2013.01); *B01L 2200/0642* (2013.01); *B01L 2200/16* (2013.01); *B01L 2300/161* (2013.01); *C12Q 2600/16* (2013.01)

(58) Field of Classification Search
CPC ............................. C12Q 1/686; B01L 3/50857
See application file for complete search history.

(56) References Cited

U.S. PATENT DOCUMENTS

| | | | | |
|---|---|---|---|---|
| 2011/0092373 A1* | 4/2011 | Colston, Jr. | ........... | B01F 3/0807 506/2 |
| 2015/0299768 A1* | 10/2015 | Ng | ...................... | C12Q 1/6806 506/23 |

FOREIGN PATENT DOCUMENTS

CN          101851652 A   * 10/2010   ............. C12Q 1/686

OTHER PUBLICATIONS

Shao, Ning, et al., Visual Detection of Multiple Genetically Modified Organisms in a Capillary Array, Jan. 6, 2017, Lab Chip, 2017, 17, 521-529. (Year: 2017).*
Li, Yang, et al., A Universal Multiplex PCR Strategy for 100-plex Amplification Using a Hydrophobically Patterned Microarray, Sep. 9, 2011, Lab Chip, 2011, 11, 3609-3618. (Year: 2011).*
Zhang, Chunsun, et al., PCR Microfluidic Devices for DNA Amplification, Dec. 2, 2005, Biotechnol. Adv., 24(3) 243-284. (Year: 2006).*

* cited by examiner

*Primary Examiner* — Angela M. Bertagna
*Assistant Examiner* — Carolyn L Greene (57) ABSTRACT

A high-throughput and rapid nucleic acids detection method based on capillary microarrays comprises the steps that firstly, microarray containing a number of hydrophilic and vertical micro-channels is fabricated by capillary assembling, casting and machining, and the outer surface of the capillary array is coated with super-hydrophobic Ultra-Ever Dry paint; secondly, different primer sets are individually loaded into the micro-channels and air-dried to adhere them on the inner surface, and then the microarray is anchored into a reaction tube; thirdly, the reaction mixture is introduced into every microchannel at once through capillary force by a special designed sample-loading adaptor, and then the amplification reaction is performed in the temperature control device; and finally, the fluorescence can either be measured continually during the reaction for real-time detection or be recorded once in the end for endpoint detection. Moreover, the products can also be recovered for other use later.

14 Claims, 3 Drawing Sheets

Specification includes a Sequence Listing.

HIGH-THROUGHPUT AND RAPID NUCLEIC ACIDS DETECTION METHOD BASED ON CAPILLARY MICROARRAYS

CROSS REFERENCE OF RELATED APPLICATION

This is a U.S. National Stage under 35 U.S.C. 371 of the International Application PCT/CN2016/078408, filed Apr. 2, 2016, which claims priority under 35 U.S.C. 119(a-d) to CN 201510901558.1, filed Dec. 8, 2015.

BACKGROUND OF THE PRESENT INVENTION

Field of Invention

The present invention relates to a detection method in the biomedical field, which is a high-throughput and rapid nucleic acids detection method based on capillary microarrays.

Description of Related Arts

Portable and rapid detection methods for nucleic acids (DNA/RNA) are widely and urgently needed in rapid diagnosis of infectious diseases, entry-exit inspection and quarantine, on-site inspection of transgenic crops and products, on-site detection of food-sourced microorganisms, identification of evidences at crime scenes, and biological anti-terrorism. (Yager P., et al, 2008, Annu. Rev. Biomed. Eng., 10, 107-144; Niemz A., et al, 2010, Trends in Biotechnology, 29, 240-250). The conventional commercial nucleic acids detection platforms are mostly based on traditional PCR (Polymerase Chain Reaction) or real-time quantitative PCR technology, which are performed in PCR tubes or 96-well PCR plates. However, there are some problems in utilization, such as the large size of the instrument, not easy to carry, high power consumption, complicated operation and low throughput (only one target can be detected in each reaction), which are difficult to meet actual needs.

With the development of microfabrication technologies, microchip platforms, including microarray chips and microfluidic chips, are increasingly used in various biochemical reactions including nucleic acids amplification and detection. Numerous nucleic acids amplification and detection methods based on microarray chips and microfluidic chips are available now (Ahmad, F., et al., 2012, Analytica chimica acta, 733, 1-15; Asiello, P J, et al., 2011, Lab on a Chip, 11, 1420-1430), and some of them enable multiple detections. For example, Li et al. used a micro-well chip to achieve a 100-fold PCR amplification (Li Y., et al., 2011, Lab on a chip 11.21, 3609-3618); Guo et al. used a microfluidic droplet chip combined with capillary electrophoresis to achieve PCR amplifications of more than 20 folds (Guo J., et al., 2011, Analytical chemistry, 83.5, 1579-1586); Fang et al. used a PDMS microfluidic chip and loop-mediated isothermal amplification to achieve the detection of 10 types of nucleic acid targets in parallel (Fang, X., et al., 2010, Analytical chemistry, 83, 690-695). Although the above-mentioned nucleic acids amplification and detection platforms based on microarray chips and microfluidic chips greatly reduce the volume of the reaction and thus reduce the consumption of reagents and samples, meanwhile the portability and throughput has also been improved, there are still some problems, such as complex production process, difficult to standardize, high cost, complicated operation and specialized equipment, which limit their practicality.

Capillary is a good biochemical reaction cell, which has low cost and large specific surface area to improve the efficiency of biochemical reactions (Mastichiadis C., et al., 2008, Trends in Analytical Chemistry 27.9, 771-784). Moreover, capillary forces facilitate the self-powered sample loading. Furthermore, capillaries are easy to integrate into microarrays for multiplex reactions and assays. Due to their excellent properties, capillaries have been widely used in the fields of gas chromatography (Ballschmiter, K., & Zell, M. 1980, Fresenius' Journal of Analytical Chemistry, 302, 20-31), capillary electrophoresis (Ewing A., et al, 1989, Anal. Chem., 61, 292-303), and protein detection (Cao Y., 2015, Journal of fluorescence, 25, 563-568).

Recently, researchers have successfully achieved the nucleic acids amplification in capillaries. For example, Manage et al. achieved PCR amplification in capillary gels (Manage D., et al, 2013, Lab Chip, 13, 2576-2584); McCarthy et al. used the padlock probe and RCA (Rolling Circle Amplification) to successfully amplify and detect two viruses in capillaries (McCarthy, E., et al., 2006, Analytical and bioanalytical chemistry, 386, 1975-1984). Zhang et al. achieved rapid detection of SNPs in the blood, which applied LAMP (loop-mediated isothermal amplification) technique in capillaries (Zhang L., et al, 2014, Anal. Chem., 86, 10461-10466). Liu et al. used LAMP technology to achieve parallel detection of multiple samples of *M. tuberculosis* in a capillary array. All of these methods took advantages of the capillaries, reduced the consumption of reagents and samples, decreased energy consumption and increased portability. However, it is still difficult for them to achieve parallel detection of more targets in a single reaction.

Combining the multiple reaction platform based on capillary microarrays with conventional nucleic acids detection technology will be a good solution for high-throughput and rapid nucleic acids detection.

SUMMARY OF THE PRESENT INVENTION

The objective of the present invention is to provide a high-throughput and rapid nucleic acids detection method based on capillary microarrays. In particular, it is a high-throughput nucleic acids detection method based on capillary microarrays for improving the throughput and efficiency of detection, and reducing cost and sample consumption. This method is applicable to various nucleic acids detection fields.

The present invention constructs a set of multiplex reaction platform based on capillary microarrays, which can realize rapid and parallel introduction of nucleic acids reagents and fast amplification reactions in a very small system. Compared with the conventional methods, the present invention has unique advantages such as high-throughput detection, simple experimental operation, low sample consumption, low detection cost, and no expensive equipment. It can be widely applied in the fields of rapid diagnosis of infectious diseases, entry-exit inspection and quarantine, on-site detection of transgenic crops and products, on-site detection of food-sourced microorganisms, identification of evidences at crime scenes, and biological anti-terrorism.

The purpose of the present invention is achieved through the following technical solutions:

The present invention relates to a high-throughput and rapid nucleic acid detection method based on capillary microarrays, wherein the characteristics comprise the following procedures:

in a first step, individually loading different primer sets into corresponding micro-channels of the capillary microarrays and air-drying, and then anchoring each of the capillary microarrays in a transparent reaction tube;

in a second step, introducing a reaction mixture except for primers into all the micro-channels to form a nucleic acid amplification system and sealing the reaction tube;

in a third step, performing an amplification reaction in a temperature control device; and in a fourth step, measuring fluorescence continually during reaction for real-time detection, or only one measurement in an end for endpoint detection.

Preferably, in the first step, the effect of the drying is to adhere nucleic acids amplification primers on the inner surface of the micro-channels.

Preferably, in the first step, the primer sets comprise: ordinary PCR primers, real-time PCR primers, loop-medicated isothermal amplification primers, rolling circle amplification primers, and recombinase polymerase primers;

wherein, when a nucleic acid amplification primers are real-time PCR primers, the primers are added to the micro-channels together with corresponding probes.

Preferably, in the first step, each of the capillary microarrays also comprises a substrate;

wherein, a plurality of the micro-channels in each of the capillary microarrays are arranged in an array on the substrate, and a small portion of the micro-channels is exposed on a surface of the substrate. An upper surface of the substrate, an outer surface of the micro-channels exposed on the substrate, and an inner surface of a bottom of the micro-channels are all hydrophobic.

The hydrophobic surface can be achieved by applying a layer of hydrophobic coating on the corresponding surface.

Preferably, in the first step, the method for obtaining the capillary microarrays includes one-time processing or assembling the capillary microarray substrate with the micro-channels; further, the processing molding includes molding, casting or machining.

Further preferably, the material of the substrate includes plastic, glass, metal, and other polymer materials; Wherein, the other polymer materials are polydimethylsiloxane, polymethyl methacrylate, polytetrafluoroethylene, Rubber, etc.; Micro-channels are hydrophilic capillaries, and the portion of the micro-channels exposed on the substrate and the bottom surface of the micro-channels are hydrophobic, but the micro-channels itself are made of hydrophilic materials.

Preferably, in the first step, the primer sets are dissolved in a cross-linking agent and then added to the micro-channels;

wherein, the cross-linking agent is one of following three mixed liquids:

a. a mass percentage of chitosan in acetic acid aqueous solution is 0.1-1%, and a pH is 4.5-6.0;

b. a mass percentage of gelatin aqueous solution is 0.1-1%; and c. a mass percentage of polyethylene glycol aqueous solution is 0.05%-5%.

Preferably, in the second step, the reaction mixture is introduced into all the micro-channels through inverted capillary forces.

Further, the reaction mixture is introduced into all the micro-channels by a special sample-loading adaptor;

wherein, the sample-loading adaptor includes a sample cell and a handle, and the handle is connected to a bottom of the sample cell; the sample cell has a smaller outer cross-section than an inner cross-section of the reaction tube; an inner cross-section of the sample cell is larger than a cross-section of each of the capillary microarrays; a depth of the sample cell is slightly less than a height of a portion of the micro-channels exposed on the surface of the substrate. An inner surface of the sample cell is hydrophilic. (See FIG. 3 for a schematic diagram of the sample-loading process)

Preferably, in the second step, the inverted capillary forces mean that inserting a sample cell filled with solutions of nucleic acids amplification reaction downwards into a reaction tube, and the solutions quickly fill the hydrophilic channels through the contact of the top of the inner wall, and then the sample-loading device is removed.

Preferably, in the fourth step, the measurement can be performed by means of a fluorescence detection device or a photometric detection device, or it may be visually recognized by differences in color or brightness. Specifically, the light source of the corresponding emission wavelength is used to irradiate the reactants in the microchannel before each measurement, and then the measurement is performed.

Preferably, the recoverable product obtained in the fifth step can be used for subsequent other tests. Specifically, it means that the product in a specific capillary can be recovered separately or all the products in the capillaries can be recovered at one time, and furtherly used for detection methods of agarose gel electrophoresis, nucleic acid hybridization, DNA chip and DNA sequencing.

Preferably, in the method, the temperature control device in the fourth step and the measurement in the fifth step can be integrated into an automation device, which is controlled by software program for its automatic operation.

Preferably, the method can be implemented individually in a single reaction tube, and it also can be implemented in parallel in an integrated 8-tube, 96-well, or 384-well plate.

Compared with the conventional technologies, the present invention has the following advantages:

1. Using capillary microarrays and hydrophilic-hydrophobic properties, the specially designed sample-loading device (see FIG. 3) can rapidly and conveniently add the reaction solutions to all micro-channels at once, thus improving the throughput and efficiency of detection in one test;

2. The use of micro-channels as the reaction chamber also greatly reduces the consumption of reagents and samples, thereby reducing the detection cost;

3. The present invention can be applied to various fields of high-throughput and rapid nucleic acids detection, such as rapid detection of infectious diseases, entry-exit inspection and quarantine, food safety and genetically modified organism (GMO) detection, and forensic identification.

BRIEF DESCRIPTION OF THE DRAWINGS

Other features, purposes, and advantages of the present invention will become more apparent by reading the detailed description of the non-limiting embodiments with reference to the accompanying drawings.

wherein "21" indicates a microchannel, "22" indicates a hydrophobic surface on the top of the substrate, and "23" indicates a substrate.

wherein "31" indicates a hydrophilic sample cell in the sample-loading device, "32" indicates the handle in the sample-loading device, "33" indicates the reaction tube, and "34" indicates the capillary microarray.

wherein "1-10" indicates P-CaMV35S, bar, CP4 epsps, P-FMV35S, pat, T-nos, nptII, ADH1, blank control, blank control, respectively.

DETAILED DESCRIPTION OF THE PREFERRED EMBODIMENT

The present invention will be described in detail below with reference to specific embodiments. The following embodiments will help those skilled in this field to further understand the present invention, but do not limit the present invention in any form. It should be noted that ordinary technicians in this field can also make several variations and improvements without departing from the concept of this invention. These are all within the protection scope of this invention.

Embodiment 1: Multiple Detection of Known Transgenic Materials Using Loop-Mediated Isothermal Amplification (LAMP)

For seven genetically modified elements and endogenous reference genes of corn commonly detected in the current transgenic products, we consulted the relevant literatures to find LAMP primer sets for these genes. All primers were synthesized by Invitrogen company (Shanghai). All primers were screened by routine LAMP reactions with calcein dyes, and a set of LAMP primers was screened for each gene that could be successfully detected. Specific primer information is shown in Table I below:

TABLE 1

| Gene | Name | Primers and probes (5'-3') |
|---|---|---|
| P-CaMV35S | FIP (SEQ ID NO. 1) | TGCGTCATCCCTTACGTCAGTGAAGAAGACGTTCCAACCACG |
| | BIP (SEQ ID NO. 2) | TCCTTCGCAAGACCCTTCCTCTGTCAGCTTGTCAGCGTGT |
| | Loop F (SEQ ID NO. 3) | GAGATATCATATCAATCCACTTGCTTTGAAGA |
| | Loop B (SEQ ID NO. 4) | ATATAAGGAAGTTCATTTCATTTGGAGAGG |
| | F3 (SEQ ID NO. 5) | CAAAGATGGACCCCCACC |
| | B3 (SEQ ID NO. 6) | CGGACCATGGAGATCTGCTA |
| bar | FIP (SEQ ID NO. 7) | TGCTGAAGTCCCTGGAGGCACAGTTGGGCAGCCCGATG |
| | BIP (SEQ ID NO. 8) | TGGCGGGGGGAGACGTACAGGGTCCCTGGAAGGCA |
| | Loop F (SEQ ID NO. 9) | GGGCTTCAAGAGCGTGGTCGCTGT |
| | Loop B (SEQ ID NO. 10) | CGGTTGACTCGGCCGTCCAGTCGTAGGCGTTGCG |
| | F3 (SEQ ID NO. 11) | TGCATGCGCACGCTC |
| | B3 (SEQ ID NO. 12) | AGGTGGACGGCGAGGT |
| CP4 epsps | FIP (SEQ ID NO. 13) | AGCAGAACAGCGGACTTCACTTCCAACGCCAATCACCTACA |
| | BIP (SEQ ID NO. 14) | ACACCCCAGGTATCACCACTGTGCACCAAAACCTTGAAGCAT |
| | Loop F (SEQ ID NO. 15) | GAGCGGAAGCCATAGGTACCC |
| | Loop B (SEQ ID NO. 16) | TATCGAGCCAATCATGACTCTGACCACACTGAAAAG |
| | F3 (SEQ ID NO. 17) | CTTGCGTGGACCAAAGACT |
| | B3 (SEQ ID NO. 18) | ACACCGTCAGCATCAGTCT |
| P-FMV35S | FIP (SEQ ID NO. 19) | GCTGGAACAGTAGTTTACTTTGACCATTAGCCAAAGCTACA |
| | BIP (SEQ ID NO. 20) | ACATGCATGGTCAGTAAGATTACTTTCAAAGATGCCCAC |
| | Loop F (SEQ ID NO. 21) | ATTGAAGATTCTTCATTGATCTCC |
| | Loop B (SEQ ID NO. 22) | GTTTCAGAAAAAGACATCCACCGAAGACTTAAAGTTA |
| | F3 (SEQ ID NO. 23) | GTCAGGGTACAGAGTCTCC |
| | B3 (SEQ ID NO. 24) | GCTGCTCGATGTTGACAA |
| pat | FIP (SEQ ID NO. 25) | TACCCCGGGCTGTGTATCCCATAGGCCTTCCAAACGATCC |
| | BIP (SEQ ID NO. 26) | ATTGCGCGCAGCTGGATACAAGGAGGAGCTGGCAACTCA |
| | Loop F (SEQ ID NO. 27) | AAGCCTCATGCAACCTAACAGAT |
| | Loop B (SEQ ID NO. 28) | GCATGGTGGATGGCATGATGTTGGTTTTTGGCAAAGGGA |
| | F3 (SEQ ID NO. 29) | GGCGCAAGGTTTTAAGTCTG |
| | B3 (SEQ ID NO. 30) | GGTAACTGGCCTAACTGGC |
| T-NOS | FIP (SEQ ID NO. 31) | AGATGGGTTTTTATGATTAGATTTATCCTAGTTTGCGC |
| | BIP (SEQ ID NO. 32) | TAATTCAACAGAAATTATATGAAGTTTCTTAAGATTGAATCCTG |
| | Loop F (SEQ ID NO. 33) | AGTCCCGCAATTATACATTTAATACGCGATAGAAAACAAAATATA |
| | Loop B (SEQ ID NO. 34) | ATAATCATCGCAAGACCGGCAA |
| | F3 (SEQ ID NO. 35) | CATAGATGACACCGCG |
| | B3 (SEQ ID NO. 36) | GATCGTTCAAACATTTGG |
| NptII | FIP (SEQ ID NO. 37) | TAGCCGGATCAAGCGTATGC TCATCTCACCTTGCTCCT |
| | BIP (SEQ ID NO. 38) | CCATTCGACCACCAAGCGA CATCCTGATCGACAAGACC |
| | Loop F (SEQ ID NO. 39) | TTGCATCAGCCATGATGGATA |
| | Loop B (SEQ ID NO. 40) | CGTACTCGGATGGAAGCC |
| | F3 (SEQ ID NO. 41) | CTCGACGTTGTCACTGAAG |
| | B3 (SEQ ID NO. 42) | TGATGCTCTTCGTCCAGA |
| ADH1 | FIP (SEQ ID NO. 43) | CCCCTCCGCAAATCTTCGAACAGTTTTGTAACTGGTGAAGGACTGAG |
| | BIP (SEQ ID NO. 44) | GGTGATCAAGTGCAAAGGTCTTTTCATAAACCAAGATTAGTCAGATCAAG |
| | Loop F (SEQ ID NO. 45) | CGCCTTGTTTCTCCTCTGTC |

TABLE 1-continued

| Gene | Name | Primers and probes (5'-3') |
|---|---|---|
| | Loop B (SEQ ID NO. 46) | CCAAATCATCCACTCCGAGAC |
| | F3 (SEQ ID NO. 47) | CTTTGGATCGATTGGTTTC |
| | B3 (SEQ ID NO. 48) | CCCAAAATTACTCAACG |

The seed powder of the conventional transgenic corn event MON863 in the laboratory was extracted and purified using a commercial DNA extraction kit, and the concentration of DNA was verified using the NanoDrop 1000 as a sample to be tested.

Figure 1:
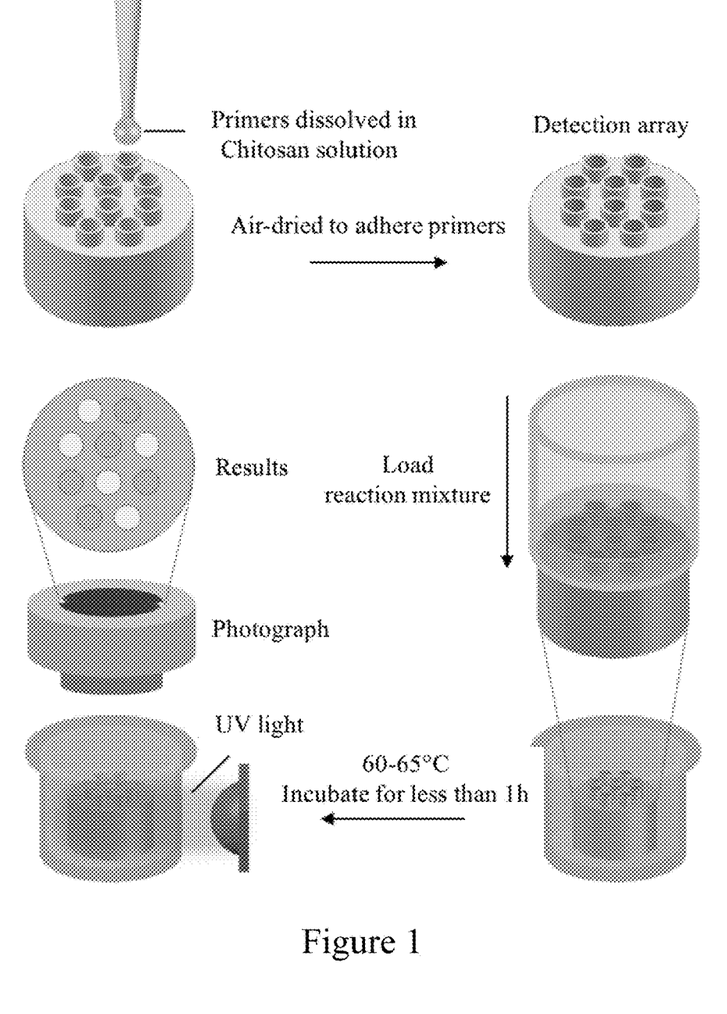
FIG. 1 is a working flowchart of embodiment 1 of the present invention.
Figure 2:
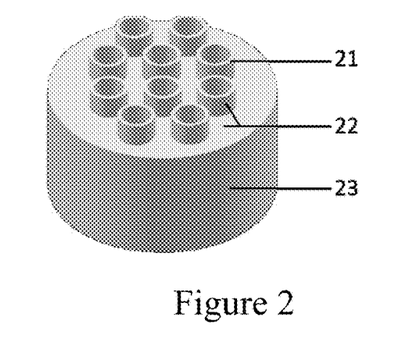
FIG. 2 shows a capillary microarray.

Multiple LAMP reactions are performed using a capillary microarray (see FIG. 2, specifically including the microchannel "21" and the substrate "23"; the top surface of the substrate "23" and the portion of the microchannel that exposes to the top surface of the substrate "22" are hydrophobic). That is, 8 sets of LAMP primers were added to each capillary in the array and air-dried to adhere them (microchannels "1-10" in the microarray indicates P-CaMV35S, bar, CP4 epsps, P-FMV35S, pat, T-nos, nptII, ADH1, blank control, blank control, respectively). The LAMP reaction system containing the DNA template is introduced into all micro-channels through inverted capillary forces to perform multiple LAMP reactions. Each reaction system only has the volume of 1.6 μL. The specific operational process is shown in FIG. 1.

Figure 3:
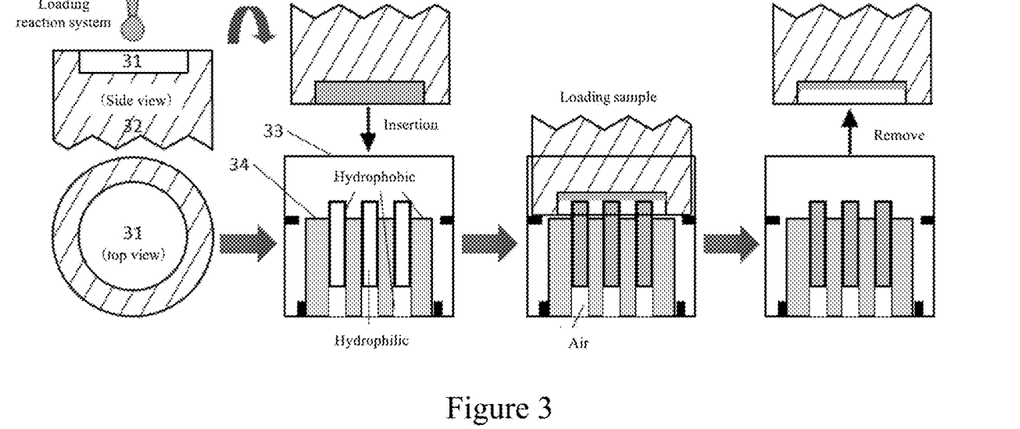
FIG. 3 is a schematic diagram of the principle of sample-loading.

The specific sample-loading process is shown in FIG. 3. The sample-loading device includes a sample cell "31" and a handle "32". The handle "32" is connected to the bottom of the sample cell "31". The sample cell "31" has a smaller outer cross-section than the inner cross-section of the reaction tube. The inner cross-section of the sample cell "31" is larger than the cross-section of the capillary microarray, and the depth of the sample cell "31" is slightly less than the height of the portion of the micro-channels exposed on the surface of the substrate. The inner surface of the sample cell "31" is hydrophilic. When the sample is loaded, the sample cell "31" filled with the LAMP reaction system containing the DNA template is inserted downwards into a reaction tube, and the solutions quickly fill the hydrophilic channels through the contact of the top of the inner wall, and then the sample-loading device is removed.

Other reaction conditions not explicitly given are all conventional nucleic acid amplification conditions.

Results detection and analysis. After the reaction is completed, a hand-held UV lamp emitting at a wavelength of 365 nm is used to irradiate the reaction tube from the side and excite the fluorescent reactants in the microchannel, and then the fluorescence signal in each capillary is photographed from the top of the reaction tube. The photo was converted to a 16-bit TIFF format by using Photoshop 7.0 (Adobe Systems Inc., USA), and the specific fluorescence intensity in each capillary was read by using a GenePix Pro 6.1 (Molecular Devices, USA).

Figure 4:
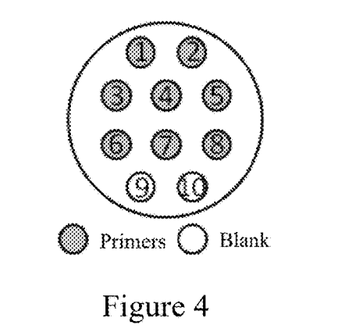
FIG. 4 is a schematic diagram of the primers arrangement pattern in embodiment 1 and embodiment 2.
Figure 5:
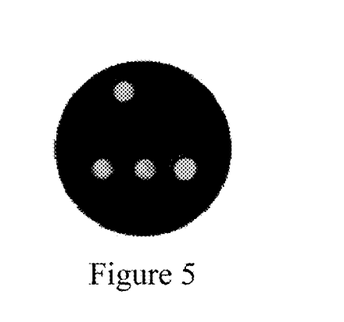
FIG. 5 is a schematic diagram of the results of embodiment 1.

According to FIG. 5, combined with the pattern diagram 4, we can see that the positive signals are marked as "1", "6", "7", and "8", which represents P-CaMV35s, T-nos, nptII, and ADH1 (endogenous genes of corn), respectively. With reference to relevant databases and literatures, theoretically, the genetic elements and endogenous genes contained in the transgenic corn were all detected at once in the multiple LAMP reaction based on a capillary microarray. For two replicates of the same sample, the results were exactly the same, and all were consistent with expectations.

Embodiment 2: Multiplex Detection of Unknown Transgenic Materials

Figure 6:
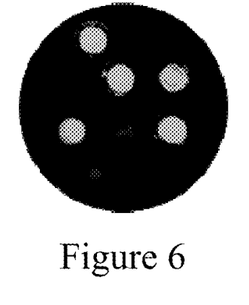
FIG. 6 is a schematic diagram of the results of embodiment 2.

Using the above-mentioned experimental procedures, the M2, a corn sample with unknown composition collected from Shanghai Port by the Shanghai Entry-Exit Inspection and Quarantine Bureau, was tested. The detection results are shown in FIG. 6; According to FIG. 6, combined with the pattern diagram FIG. 4, we can see that the positive signals are marked as "1", "4", "5", "6", and "8", which represents P-CaMV35s, FMV-35S, pst, T-nos, and ADH1 (endogenous genes of corn), respectively. Comparing this results with the results of an independent real-time PCR, we found that the detected target is completely consistent, so the detection method can be considered to have high specificity and accuracy. The real-time PCR results are as follows:

TABLE 2

| | | Ct Value | |
|---|---|---|---|
| Targets | Replicates | M2 | Control (no template) |
| P-CaMV35s | 1 | 29.94 | not detected |
| | 2 | 29.40 | not detected |
| | 3 | 29.84 | not detected |
| | Mean | 29.73 | not detected |
| bar | 1 | not detected | not detected |
| | 2 | not detected | not detected |
| | 3 | not detected | not detected |
| | Mean | not detected | not detected |
| cp4 epsps | 1 | not detected | not detected |
| | 2 | not detected | not detected |
| | 3 | not detected | not detected |
| | Mean | not detected | not detected |
| FMV-35S | 1 | 29.34 | not detected |
| | 2 | 28.99 | not detected |
| | 3 | 28.81 | not detected |
| | Mean | 29.04 | not detected |
| Pat | 1 | 27.71 | not detected |
| | 2 | 27.94 | not detected |
| | 3 | 28.67 | not detected |
| | Mean | 28.11 | not detected |
| T-nos | 1 | 28.48 | not detected |
| | 2 | 28.30 | not detected |
| | 3 | 28.31 | not detected |
| | Mean | 28.36 | not detected |
| nptII | 1 | not detected | not detected |
| | 2 | not detected | not detected |
| | 3 | not detected | not detected |
| | Mean | not detected | not detected |
| ADH1 | 1 | 29.38 | not detected |
| | 2 | 29.37 | not detected |
| | 3 | 29.11 | not detected |
| | Mean | 29.29 | not detected |

The specific embodiments of the present invention have been described above. It should be understood that the present invention is not limited to the specific implementation manners above, and technicians in this field can also make several variations and improvements within the scope of the claims, which would not affect the essence of this invention.

What is claimed is:

1. A high-throughput and rapid nucleic acids detection method based on capillary microarrays, comprising steps of:
   in a first step, individually loading different primer sets into corresponding capillaries of the capillary microarrays and air-drying to adhere the different primer sets on an inner surface, and then anchoring each of the capillary microarrays into a reaction tube;
   in a second step, introducing a reaction mixture without primers into all the capillaries by a sample-loading adaptor to form a nucleic acid amplification system; wherein the sample-loading adaptor comprises a sample cell and a handle, and the handle is connected to a bottom of the sample cell;
   the sample cell has a smaller outer cross-section than an inner cross-section of the reaction tube; an inner cross-section of the sample cell is larger than a cross-section of each of the capillary microarrays; and the depth of the sample cell is less than a height of a portion of the capillaries exposed on a surface of the substrate;
   in a third step, performing an amplification reaction in a temperature control device; and
   in a fourth step, measuring fluorescence either continually during the amplification reaction for real-time detection, or once at the end of the amplification reaction for endpoint detection.

2. The high-throughput and rapid nucleic acids detection method based on the capillary microarrays according to claim 1, wherein in the first step, the primer sets comprise: endpoint PCR primers, real-time PCR primers, loop-mediated isothermal amplification primers, rolling circle amplification primers, or recombinase polymerase primers;
   wherein, when the primer sets are real-time PCR primers, the real-time PCR primers are added to the capillaries together with corresponding probes.

3. The high-throughput and rapid nucleic acids detection method based on the capillary microarrays according to claim 1, wherein in the first step, each of the capillary microarrays also comprises a substrate;
   wherein, a plurality of the capillaries in each of the capillary microarrays are arranged in an array on the substrate, and a small portion of the capillaries is exposed on a surface of the substrate.

4. The high-throughput and rapid nucleic acids detection method based on the capillary microarrays according to claim 3, wherein an upper surface of the substrate, an outer surface of the capillaries exposed on the substrate, and an inner surface of a bottom of the capillaries are all hydrophobic; and the remaining surfaces of the capillaries are hydrophilic.

5. The high-throughput and rapid nucleic acids detection method based on the capillary microarrays according to claim 1, wherein in the first step, the primer sets are dissolved in a cross-linking agent and then added to the capillaries;
   wherein, the cross-linking agent is one of following three mixed liquids:
   (a) an aqueous acetic acid solution with a pH of 4.5 to 6.0 and containing chitosan at a mass percentage of 0.1-1%;
   (b) an aqueous solution containing gelatin at a mass percentage of 0.1-1%; and
   (c) an aqueous solution containing polyethylene glycol at a mass percentage of 0.05%-5%.

6. The high-throughput and rapid nucleic acids detection method based on the capillary microarrays according to claim 1, wherein in the second step, the reaction mixture is introduced into all the capillaries through inverted capillary forces.

7. The high-throughput and rapid nucleic acids detection method based on the capillary microarrays according to claim 1, wherein an inner surface of the sample cell is hydrophilic.

8. The high-throughput and rapid nucleic acids detection method based on the capillary microarrays according to claim 1, wherein the method is implemented individually in a single reaction tube.

9. The high-throughput and rapid nucleic acids detection method based on the capillary microarrays according to claim 2, wherein the method is implemented individually in a single reaction tube.

10. The high-throughput and rapid nucleic acids detection method based on the capillary microarrays according to claim 3, wherein the method is implemented individually in a single reaction tube.

11. The high-throughput and rapid nucleic acids detection method based on the capillary microarrays according to claim 4, wherein the method is implemented individually in a single reaction tube.

12. The high-throughput and rapid nucleic acids detection method based on the capillary microarrays according to claim 5, wherein the method is implemented individually in a single reaction tube.

13. The high-throughput and rapid nucleic acids detection method based on the capillary microarrays according to claim 6, wherein the method is implemented individually in a single reaction tube.

14. The high-throughput and rapid nucleic acids detection method based on the capillary microarrays according to claim 7, wherein the method is implemented individually in a single reaction tube.

\* \* \* \* \*

SEQUENCE LISTING

<160> NUMBER OF SEQ ID NOS: 48

<210> SEQ ID NO 1
<211> LENGTH: 42
<212> TYPE: DNA
<213> ORGANISM: Artificial Sequence
<220> FEATURE:
<223> OTHER INFORMATION: P-CaMV35S FIP

<400> SEQUENCE: 1
tgcgtcatcc cttacgtcag tgaagaagac gttccaacca cg         42

<210> SEQ ID NO 2
<211> LENGTH: 40
<212> TYPE: DNA
<213> ORGANISM: Artificial Sequence
<220> FEATURE:
<223> OTHER INFORMATION: P-CaMV35S BIP

<400> SEQUENCE: 2
tccttcgcaa gaccctctcct ctgtcagctt gtcagcgtgt           40

<210> SEQ ID NO 3
<211> LENGTH: 32
<212> TYPE: DNA
<213> ORGANISM: Artificial Sequence
<220> FEATURE:
<223> OTHER INFORMATION: P-CaMV35S Loop F

<400> SEQUENCE: 3
gagatatcat atcaatccac ttgctttgaa ga                    32

<210> SEQ ID NO 4
<211> LENGTH: 30
<212> TYPE: DNA
<213> ORGANISM: Artificial Sequence
<220> FEATURE:
<223> OTHER INFORMATION: P-CaMV35S Loop B

<400> SEQUENCE: 4
atataaggaa gttcatttca tttggagagg                       30

<210> SEQ ID NO 5
<211> LENGTH: 32
<212> TYPE: DNA
<213> ORGANISM: Artificial Sequence
<220> FEATURE:
<223> OTHER INFORMATION: P-CaMV35S F3

<400> SEQUENCE: 5
gagatatcat atcaatccac ttgctttgaa ga                    32

<210> SEQ ID NO 6
<211> LENGTH: 30
<212> TYPE: DNA
<213> ORGANISM: Artificial Sequence
<220> FEATURE:
<223> OTHER INFORMATION: P-CaMV35S B3

<400> SEQUENCE: 6
atataaggaa gttcatttca tttggagagg                       30

<210> SEQ ID NO 7
<211> LENGTH: 38
<212> TYPE: DNA
<213> ORGANISM: Artificial Sequence
<220> FEATURE:
<223> OTHER INFORMATION: bar FIP

<400> SEQUENCE: 7
tgctgaagtc cctggaggca cagttgggca gcccgatg					38

<210> SEQ ID NO 8
<211> LENGTH: 35
<212> TYPE: DNA
<213> ORGANISM: Artificial Sequence
<220> FEATURE:
<223> OTHER INFORMATION: bar BIP

<400> SEQUENCE: 8 tggcggggggg agacgtacag ggtccctgga aggca					35

<210> SEQ ID NO 9
<211> LENGTH: 24
<212> TYPE: DNA
<213> ORGANISM: Artificial Sequence
<220> FEATURE:
<223> OTHER INFORMATION: bar Loop F

<400> SEQUENCE: 9
gggcttcaag agcgtggtcg ctgt					24

<210> SEQ ID NO 10
<211> LENGTH: 34
<212> TYPE: DNA
<213> ORGANISM: Artificial Sequence
<220> FEATURE:
<223> OTHER INFORMATION: bar Loop B

<400> SEQUENCE: 10
cggttgactc ggccgtccag tcgtaggcgt tgcg					34

<210> SEQ ID NO 11
<211> LENGTH: 15
<212> TYPE: DNA
<213> ORGANISM: Artificial Sequence
<220> FEATURE:
<223> OTHER INFORMATION: bar F3

<400> SEQUENCE: 11
tgcatgcgca cgctc					15

<210> SEQ ID NO 12
<211> LENGTH: 16
<212> TYPE: DNA
<213> ORGANISM: Artificial Sequence
<220> FEATURE:
<223> OTHER INFORMATION: bar B3

<400> SEQUENCE: 12
aggtggacgg cgaggt					16

<210> SEQ ID NO 13
<211> LENGTH: 41
<212> TYPE: DNA
<213> ORGANISM: Artificial Sequence
<220> FEATURE:
<223> OTHER INFORMATION: CP4 epsps FIP

<400> SEQUENCE: 13
agcagaacag cggacttcac ttccaacgcc aatcacctac a					41

```
<210> SEQ ID NO 14
<211> LENGTH: 42
<212> TYPE: DNA
<213> ORGANISM: Artificial Sequence
<220> FEATURE:
<223> OTHER INFORMATION: CP4 epsps BIP

<400> SEQUENCE: 14 acacccagg tatcaccact gtgcaccaaa accttgaagc at                  42

<210> SEQ ID NO 15
<211> LENGTH: 21
<212> TYPE: DNA
<213> ORGANISM: Artificial Sequence
<220> FEATURE:
<223> OTHER INFORMATION: CP4 epsps Loop F

<400> SEQUENCE: 15
gagcggaagc cataggtacc c                                       21

<210> SEQ ID NO 16
<211> LENGTH: 37
<212> TYPE: DNA
<213> ORGANISM: Artificial Sequence
<220> FEATURE:
<223> OTHER INFORMATION: CP4 epsps Loop B

<400> SEQUENCE: 16
tatcgagcca atcatgactc gtgaccacac tgaaaag                      37

<210> SEQ ID NO 17
<211> LENGTH: 19
<212> TYPE: DNA
<213> ORGANISM: Artificial Sequence
<220> FEATURE:
<223> OTHER INFORMATION: CP4 epsps F3

<400> SEQUENCE: 17
cttgcgtgga ccaaagact                                          19

<210> SEQ ID NO 18
<211> LENGTH: 19
<212> TYPE: DNA
<213> ORGANISM: Artificial Sequence
<220> FEATURE:
<223> OTHER INFORMATION: CP4 epsps B3

<400> SEQUENCE: 18
acaccgtcag catcagtct                                          19

<210> SEQ ID NO 19
<211> LENGTH: 42
<212> TYPE: DNA
<213> ORGANISM: Artificial Sequence
<220> FEATURE:
<223> OTHER INFORMATION: P-FMV35S FIP

<400> SEQUENCE: 19
gctggaacag tagtttactt tgaccattag ccaaaagcta ca                42

<210> SEQ ID NO 20
<211> LENGTH: 39
<212> TYPE: DNA
<213> ORGANISM: Artificial Sequence
<220> FEATURE:
<223> OTHER INFORMATION: P-FMV35S BIP
```

<400> SEQUENCE: 20
acatgcatgg tcagtaagat tactttcaaa gatgcccac                               39

<210> SEQ ID NO 21
<211> LENGTH: 24
<212> TYPE: DNA
<213> ORGANISM: Artificial Sequence
<220> FEATURE:
<223> OTHER INFORMATION: P-FMV35S Loop F

<400> SEQUENCE: 21
attgaagatt cttcattgat ctcc                                              24

<210> SEQ ID NO 22
<211> LENGTH: 37
<212> TYPE: DNA
<213> ORGANISM: Artificial Sequence
<220> FEATURE:
<223> OTHER INFORMATION: P-FMV35S Loop B

<400> SEQUENCE: 22
gtttcagaaa aagacatcca ccgaagactt aaagtta                                37

<210> SEQ ID NO 23
<211> LENGTH: 19
<212> TYPE: DNA
<213> ORGANISM: Artificial Sequence
<220> FEATURE:
<223> OTHER INFORMATION: P-FMV35S F3

<400> SEQUENCE: 23
gtcagggtac agagtctcc                                                    19

<210> SEQ ID NO 24
<211> LENGTH: 18
<212> TYPE: DNA
<213> ORGANISM: Artificial Sequence
<220> FEATURE:
<223> OTHER INFORMATION: P-FMV35S B3

<400> SEQUENCE: 24
gctgctcgat gttgacaa                                                     18

<210> SEQ ID NO 25
<211> LENGTH: 40
<212> TYPE: DNA
<213> ORGANISM: Artificial Sequence
<220> FEATURE:
<223> OTHER INFORMATION: pat FIP

<400> SEQUENCE: 25
taccccgggc tgtgtatccc ataggccttc caaacgatcc                             40

<210> SEQ ID NO 26
<211> LENGTH: 39
<212> TYPE: DNA
<213> ORGANISM: Artificial Sequence
<220> FEATURE:
<223> OTHER INFORMATION: pat BIP

<400> SEQUENCE: 26
attgcgcgca gctggataca aggaggagct ggcaactca                              39

<210> SEQ ID NO 27

```
<211> LENGTH: 23
<212> TYPE: DNA
<213> ORGANISM: Artificial Sequence
<220> FEATURE:
<223> OTHER INFORMATION: pat Loop F

<400> SEQUENCE: 27
aagcctcatg caacctaaca gat                                              23

<210> SEQ ID NO 28
<211> LENGTH: 39
<212> TYPE: DNA
<213> ORGANISM: Artificial Sequence
<220> FEATURE:
<223> OTHER INFORMATION: pat Loop B

<400> SEQUENCE: 28
gcatggtgga tggcatgatg ttggtttttg gcaaaggga                             39

<210> SEQ ID NO 29
<211> LENGTH: 20
<212> TYPE: DNA
<213> ORGANISM: Artificial Sequence
<220> FEATURE:
<223> OTHER INFORMATION: pat F3

<400> SEQUENCE: 29
ggcgcaaggt tttaagtctg                                                  20

<210> SEQ ID NO 30
<211> LENGTH: 19
<212> TYPE: DNA
<213> ORGANISM: Artificial Sequence
<220> FEATURE:
<223> OTHER INFORMATION: pat B3

<400> SEQUENCE: 30
ggtaactggc ctaactggc                                                   19

<210> SEQ ID NO 31
<211> LENGTH: 38
<212> TYPE: DNA
<213> ORGANISM: Artificial Sequence
<220> FEATURE:
<223> OTHER INFORMATION: T-NOS FIP

<400> SEQUENCE: 31
agatgggttt ttatgattag atttatccta gtttgcgc                              38

<210> SEQ ID NO 32
<211> LENGTH: 44
<212> TYPE: DNA
<213> ORGANISM: Artificial Sequence
<220> FEATURE:
<223> OTHER INFORMATION: T-NOS BIP

<400> SEQUENCE: 32
taattcaaca gaaattatat gaagtttctt aagattgaat cctg                       44

<210> SEQ ID NO 33
<211> LENGTH: 45
<212> TYPE: DNA
<213> ORGANISM: Artificial Sequence
<220> FEATURE:
<223> OTHER INFORMATION: T-NOS Loop F

<400> SEQUENCE: 33
```
agtcccgcaa ttatacattt aatacgcgat agaaaacaaa atata       45

<210> SEQ ID NO 34
<211> LENGTH: 22
<212> TYPE: DNA
<213> ORGANISM: Artificial Sequence
<220> FEATURE:
<223> OTHER INFORMATION: T-NOS Loop B

<400> SEQUENCE: 34
ataatcatcg caagaccggc aa       22

<210> SEQ ID NO 35
<211> LENGTH: 16
<212> TYPE: DNA
<213> ORGANISM: Artificial Sequence
<220> FEATURE:
<223> OTHER INFORMATION: T-NOS F3

<400> SEQUENCE: 35
catagatgac accgcg       16

<210> SEQ ID NO 36
<211> LENGTH: 18
<212> TYPE: DNA
<213> ORGANISM: Artificial Sequence
<220> FEATURE:
<223> OTHER INFORMATION: T-NOS B3

<400> SEQUENCE: 36
gatcgttcaa acatttgg       18

<210> SEQ ID NO 37
<211> LENGTH: 38
<212> TYPE: DNA
<213> ORGANISM: Artificial Sequence
<220> FEATURE:
<223> OTHER INFORMATION: NptII FIP

<400> SEQUENCE: 37
tagccggatc aagcgtatgc tcatctcacc ttgctcct       38

<210> SEQ ID NO 38
<211> LENGTH: 38
<212> TYPE: DNA
<213> ORGANISM: Artificial Sequence
<220> FEATURE:
<223> OTHER INFORMATION: NptII BIP

<400> SEQUENCE: 38
ccattcgacc accaagcgac atcctgatcg acaagacc       38

<210> SEQ ID NO 39
<211> LENGTH: 21
<212> TYPE: DNA
<213> ORGANISM: Artificial Sequence
<220> FEATURE:
<223> OTHER INFORMATION: NptII Loop F

<400> SEQUENCE: 39
ttgcatcagc catgatggat a       21

<210> SEQ ID NO 40
<211> LENGTH: 18
<212> TYPE: DNA

```
<213> ORGANISM: Artificial Sequence
<220> FEATURE:
<223> OTHER INFORMATION: NptII Loop B

<400> SEQUENCE: 40
cgtactcgga tggaagcc                                                 18

<210> SEQ ID NO 41
<211> LENGTH: 19
<212> TYPE: DNA
<213> ORGANISM: Artificial Sequence
<220> FEATURE:
<223> OTHER INFORMATION: NptII F3

<400> SEQUENCE: 41
ctcgacgttg tcactgaag                                                19

<210> SEQ ID NO 42
<211> LENGTH: 18
<212> TYPE: DNA
<213> ORGANISM: Artificial Sequence
<220> FEATURE:
<223> OTHER INFORMATION: NptII B3

<400> SEQUENCE: 42
tgatgctctt cgtccaga                                                 18

<210> SEQ ID NO 43
<211> LENGTH: 47
<212> TYPE: DNA
<213> ORGANISM: Artificial Sequence
<220> FEATURE:
<223> OTHER INFORMATION: ADH1 FIP

<400> SEQUENCE: 43
cccctccgca aatcttcgaa cagttttgta actggtgaag gactgag                 47

<210> SEQ ID NO 44
<211> LENGTH: 50
<212> TYPE: DNA
<213> ORGANISM: Artificial Sequence
<220> FEATURE:
<223> OTHER INFORMATION: ADH1 BIP

<400> SEQUENCE: 44
ggtgatcaag tgcaaaggtc ttttcataaa ccaagattag tcagatcaag              50

<210> SEQ ID NO 45
<211> LENGTH: 20
<212> TYPE: DNA
<213> ORGANISM: Artificial Sequence
<220> FEATURE:
<223> OTHER INFORMATION: ADH1 Loop F

<400> SEQUENCE: 45
cgccttgttt ctcctctgtc                                               20

<210> SEQ ID NO 46
<211> LENGTH: 21
<212> TYPE: DNA
<213> ORGANISM: Artificial Sequence
<220> FEATURE:
<223> OTHER INFORMATION: ADH1 Loop B

<400> SEQUENCE: 46
ccaaatcatc cactccgaga c                                             21
```

```
<210> SEQ ID NO 47
<211> LENGTH: 19
<212> TYPE: DNA
<213> ORGANISM: Artificial Sequence
<220> FEATURE:
<223> OTHER INFORMATION: ADH1 F3

<400> SEQUENCE: 47
ctttggatcg attggtttc                                              19

<210> SEQ ID NO 48
<211> LENGTH: 17
<212> TYPE: DNA
<213> ORGANISM: Artificial Sequence
<220> FEATURE:
<223> OTHER INFORMATION: ADH1 B3

<400> SEQUENCE: 48
cccaaaatta ctcaacg                                                17
```